United States Patent
Eccardt et al.

(10) Patent No.: US 6,228,029 B1
(45) Date of Patent: May 8, 2001

(54) METHOD FOR THE IDENTIFICATION OF PERSONS

(75) Inventors: Peter-Christian Eccardt, Ottobrunn; Martin Vossiek, München, both of (DE)

(73) Assignee: Siemens Aktiengesellschaft, Munich (DE)

(*) Notice: Subject to any disclaimer, the term of this patent is extended or adjusted under 35 U.S.C. 154(b) by 0 days.

(21) Appl. No.: 09/301,448

(22) Filed: Apr. 29, 1999

(51) Int. Cl.[7] ............................................. A61B 8/00
(52) U.S. Cl. ............................ 600/437; 600/443; 600/447
(58) Field of Search ................................. 600/437, 443, 600/447, 438, 439, 399

(56) References Cited

U.S. PATENT DOCUMENTS

| | | | | |
|---|---|---|---|---|
| 5,143,063 | * | 9/1992 | Fellner | 600/648 |
| 5,587,533 | * | 12/1996 | Schneider et al. | 73/614 |
| 5,709,206 | * | 1/1998 | Teboul | 600/437 |

* cited by examiner

Primary Examiner—Marvin M. Lateef
Assistant Examiner—Maulin Patel
(74) Attorney, Agent, or Firm—Schiff Hardin & Waite

(57) ABSTRACT

An identification of persons is conducted on the basis of the sweat gland channel structures in the horny layer of the skin of a finger. For that purpose, ultrasound waves are transmitted into the skin and the received echos are evaluated.

15 Claims, 1 Drawing Sheet

METHOD FOR THE IDENTIFICATION OF PERSONS

RELATED APPLICATION

The present application is related to copending application Ser. No. 08/973,806 entitled "Method For The Identification Of Persons" of the same inventors, and which was filed Dec. 9, 1997 in the U.S.

BACKGROUND OF THE INVENTION

The invention is directed to a method for the identification of persons with ultrasound.

U.S. Pat. No. 4,564,019 discloses a method for the measurement of characteristics of living tissue by ultrasound. DE 4 226 865 A1 discloses an ultrasound diagnostics apparatus for dermatology.

Imaging methods for the recognition of the ridge structure of skin surfaces are disclosed by U.S. Pat. No. 5,224,174 and WO 95/12354.

U.S. Pat. No. 4,977,601, EP 0 619 095 A1, U.S. Pat. No. 5,218,644, U.S. Pat. No. 5,258,922, EP 0 402 779 A2 and WO 94/24937 disclose methods that utilize the amount of the spatial frequency spectrum of the ridge structure or of other cell structures ("epithelium structure") not described in greater detail in the applications. These structures are acquired by a transducer section and are averaged over a plurality of transducer sections for the identification of persons.

WO 94/010434 discloses a method that combines ultrasound waves with electromagnetic waves.

WO 95/06262 discloses a method that works with inverse excitation.

SUMMARY OF THE INVENTION

It is an object of the invention to specify a method for the identification of persons that assures a reliable personal identification and that is simple to realize.

According to the present invention, a method is provided for detection of skin structures of persons including the steps of utilizing ultrasound to detect the skin structures and wherein the ultrasound detects a lateral position of channels of sweat glands in predetermined skin layers.

The invention is described further on the basis of three Figures.

DESCRIPTION OF THE PREFERRED EMBODIMENTS

The upper skin layer of the human fingertip, also referred to as the epidermis, is composed of a horny layer, of a germinal layer and of a basal layer. The boundary surface of the horny layer to the coupling medium represents a high impedance discontinuity for ultrasound and can be utilized for the recognition of the surface. The imaging methods for the recognition of the ridge structure of the skin surface known from the aforementioned prior art utilize this effect.

Figure 1:
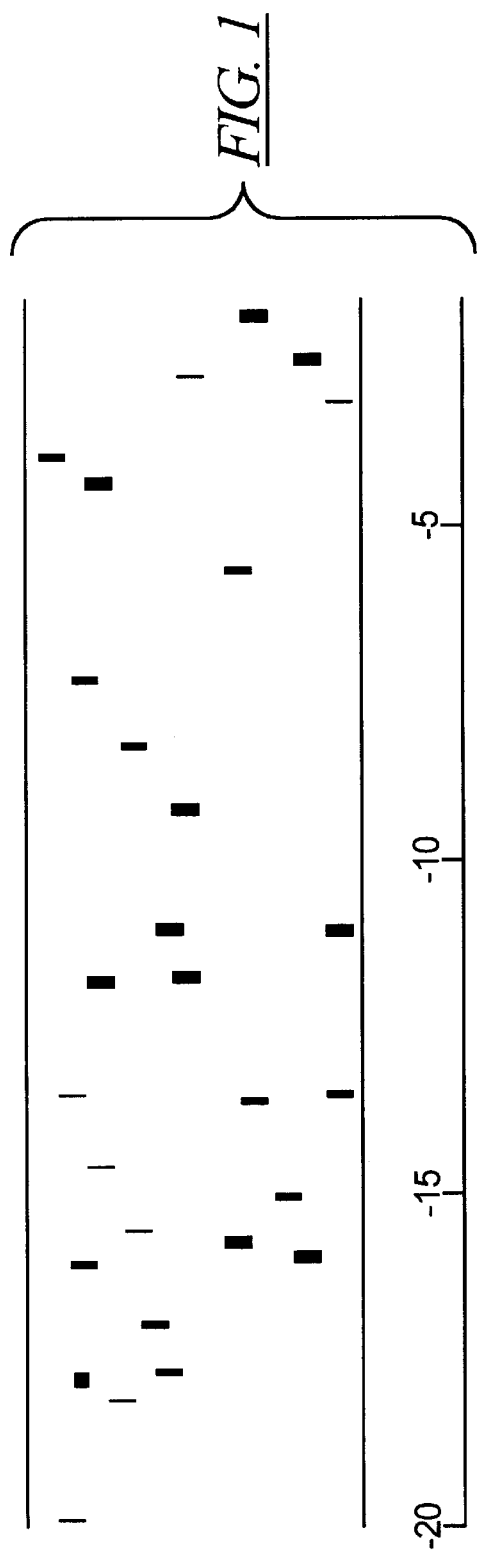
FIG. 1 is a schematic illustration of sweat pores having associated sweat glands in the horny layer below the skin surface and wherein the sweat pores are connected to the sweat glands by channels.

The horny layer is largely constant in terms of its acoustic properties and thus has a low-echo characteristic. The sweat pores associated with and connected by channels to sweat glands present in the horny layer form an exception, these usually being arranged along the furrows between the ridges. The sweat glands are capable of being acquired in a section of the ultrasound image (C-scan) in a specific depth, typically between 100 and 250 $\mu$m below the skin surface (see FIG. 1 with respect thereto).

According to the present invention, the ultrasound detects skin structures, and more specifically the lateral position of channels which connect the sweat glands and the sweat pores in the horny layer. Skin layers which are detected by ultrasound and having the channels preferably lie below the skin surface and above the transition to the skin forming layers beneath the homing layer, and typically 100 to 250 $\mu$m deep below the skin surface.

Figure 2:
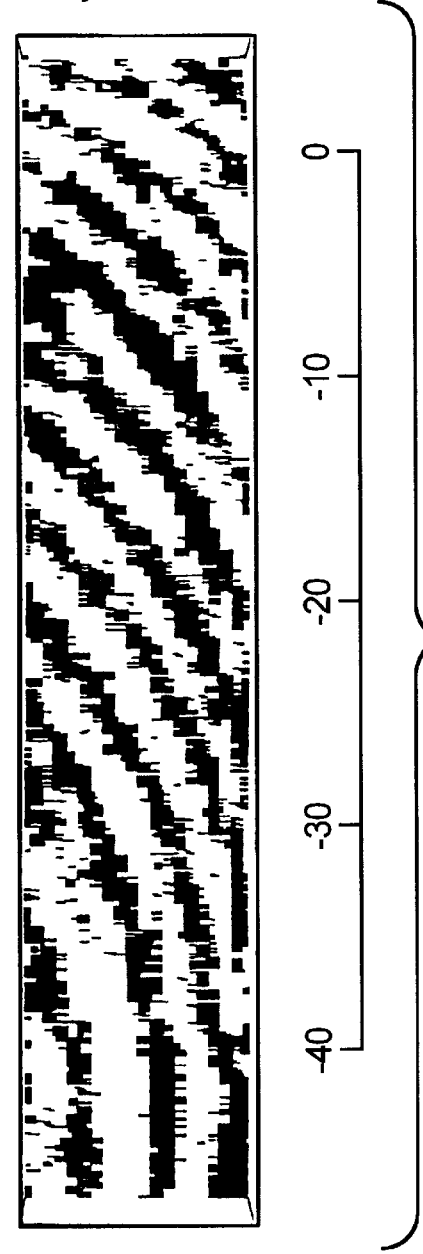
FIG. 2 is a graph illustrating the ridge structure repeating in a more deeply disposed skin layer.

The ridge structure present at the finger surface repeats in a more deeply disposed skin layer, typically 200 to 500 $\mu$m (see FIG. 2). The transition from the dead (low-water) layer of the epidermis to the hydrous, skin-forming layers structured like the finger ridges represents a clearly measurable impedance discontinuity, so that this skin layer is likewise suitable for the selection of person-specific features.

An advantage of the detection of the deeper skin layers is a higher protection against falsification and a constant recognition rate given a superficial injury to the skin.

Due to the good registered image of the surface of the skin to be achieved with ultrasound, the surface structure of the skin is constantly utilized for the identification. The additional identification on the basis of deeper skin layers, however, significantly improves the method.

A particular advantage of the detection of the lateral position of the channels running between the sweat pores and the sweat glands is that the acquired data sets can be processed with little memory requirement and calculating time because of the binary information (sweat gland channel present or not).

Figure 3:
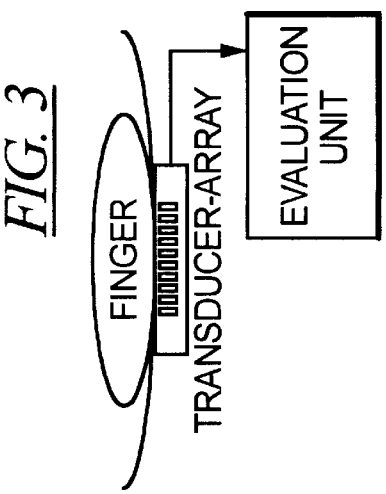
FIG. 3 shows an ultrasound transducer array connected to an evaluation unit for performing the method of the invention.

A two-dimensional ultrasound transducer array of approximately 20*20 to 200*200, and typically 100*100 ultrasound transducers, having a transducer spacing of approximately 50 through 200 $\mu$m is arranged such that the information-bearing parts of the fingertip is acquired, i.e. the region in which the ridge structure recognizable at the skin surface also comprises significant features (see FIG. 3). The echo amplitude of the skin layer to be investigated is investigated in the range from 100 through 1000 $\mu$m with a pulse-echo method. The individual transducer sections can be implemented as individual transducer sections (each transducer measures its own echo) or as separate transducer sections (one transducer transmits and one or more transducers receive).

A cost-beneficial realization derives when the echo amplitudes of only a specific depth, for example the plane of the sweat glands or the plane of the deeper, information-bearing skin layers, are stored as scalar or binary values supplied to a pattern recognition. The adaptation of the measuring depth can thereby be necessary for compensating different skin thicknesses.

Alternatively, the time position of the echo maximum can also be acquired. In the skin-forming layers that are highly reflective in addition to the skin surface, this represents a height profile that can be interpreted analogous to the surface. A cost-beneficial hardware solution is comprised in ridding the envelope of the reception signal of high-frequency parts by low-pass filtering, differentiating it and supplying it to a comparator. The time until the zero-axis crossing, i.e. until the signal maximum is reached, can be determined by stopping a counter or by measuring a voltage at a capacitor charged during the run time.

The invention uses a lateral position of the channels connecting the pores to the sweat glands of the horny layer of the human fingertip as a person-specific feature. These are detected with an ultrasound transmission/reception unit. The information deriving from the ultrasound transmission/reception unit are further-processed in the evaluation unit that follows the ultrasound transmission/reception unit.

It is likewise possible to employ the structure of the subdermal skin-forming layers under the horny layer as person-specific feature in addition to the detection of the sweat gland channel positions.

It is also likewise possible to employ, in addition to the detection of the sweat gland channel positions, the detection of an external structure of the horny layer.

It is also possible to employ a passive infrared system with a wavelength of approximately 10 µm in order to register the sweat gland channels. These represent locations of lower heat emission.

The individual ultrasound transducers of the ultrasound transducer array have a lateral resolution between 50 and 200 µm and can be micromechanically manufactured.

It is also possible to employ 2—2 composite ultrasound transducers having a lateral resolution between 50 and 200 µm.

The echo amplitudes or the maximums of the echo amplitudes in a specific skin layer can be registered and supplied to an image processing.

Although various minor modifications might be suggested by those skilled in the art, it should be understood that we wish to embody within the scope of the patent warranted hereon all such modifications as reasonably and properly come with the scope of our contribution to the art.

We claim as our invention:

1. A method for identification of a person by detecting skin structures of the person, comprising the steps of:

utilizing ultrasound to detect the skin structures to identify the person; and detecting as said skin structures a lateral position of channels connecting sweat glands to sweat pores in predetermined skin layers.

2. The method according to claim 1 wherein the sweat pores, channels, and sweat glands lie in a horny layer.

3. The method according to claim 1 wherein the channels which are detected lie in skin layers below a surface of the skin and above a transition to skin forming layers beneath a horny layer, and wherein said skin layers are between 100 to 250 µm below the skin surface.

4. The method according to claim 1 including the step of also detecting an external structure of a horny layer.

5. The method according to claim 1 including the step of also detecting subdermal skin forming layers beneath a horny layer.

6. The method according to claim 1 including the step of providing a twodimensional array of greater than 20*20 up to a maximum of 150*150 ultrasound transducers.

7. The method according to claim 6 including the step of providing 100*100 ultrasound transducers in the array.

8. The method according to claim 1 wherein a two-dimensional array of ultrasound transducers is provided having a transducer distance of 50 to 200 µm spacing.

9. The method according to claim 1 including the step of detecting a transition between a low-water horny layer and a hydrous skin-forming layers lying below the low-water horny layer.

10. The method according to claim 1 including the step of varying measuring depth for compensation of different skin thicknesses.

11. The method according to claim 1 including the step of acquiring a time position of an echo maximum, and producing an evaluatable height profile via a distance measurement.

12. The method according to claim 1 wherein detected data are supplied to a pattern recognition system.

13. The method according to claim 1 wherein detected patterns are compared to patterns from a data bank.

14. The method according to claim 1 wherein the skin structures are in a fingertip of the persons.

15. A method for identification of a person by detecting skin structures of the person, comprising the steps of:

utilizing ultrasound to detect the skin structures to identify the person; and detecting as said skin structures channels connecting sweat glands to sweat pores in predetermined skin layers.

* * * * *